United States Patent [19]

Litzie et al.

[11] Patent Number: 4,540,399
[45] Date of Patent: Sep. 10, 1985

[54] EMERGENCY BYPASS SYSTEM

[76] Inventors: Ken Litzie, 21055 Glenbrook Dr., Walnut, Calif. 91789; Craig P. Roberts, 850 A Loma Dr., Hermosa Beach, Calif. 90254

[21] Appl. No.: 463,057
[22] Filed: Feb. 1, 1983
[51] Int. Cl.³ .............................................. A61M 1/03
[52] U.S. Cl. ...................................... 607/4; 128/1 D; 604/122
[58] Field of Search ................ 604/4, 8, 5–7, 604/122–123, 151; 422/44; 210/321.2; 128/DIG. 3

[56] References Cited
U.S. PATENT DOCUMENTS

| | | | |
|---|---|---|---|
| 2,406,207 | 8/1946 | Desmet | 604/4 |
| 3,426,743 | 2/1969 | Chestnut | 604/4 |
| 3,881,483 | 5/1975 | Sausse | 604/4 |
| 3,949,734 | 4/1976 | Edwards | 128/1 D |
| 4,353,368 | 10/1982 | Slovak | 128/214 R |

Primary Examiner—Stephen C. Pellegrino
Attorney, Agent, or Firm—Poms, Smith, Lande & Rose

[57] ABSTRACT

A closed emergency heart bypass system is disclosed herein for extra-corporeal blood circulation use which employs a minimum of components arranged in a series relationship. The components include a non-occlusive blood pump aspirating venous blood from an appropriate cannula for introduction to an oxygenator and a bubble-trapping device followed by return to a patient's body via an arterial cannula. Tubing interconnects the components and a bypass loop selectively joins the tubing adjacent to the venous and arterial cannulas for air displacement during initial pump priming and tube purging. Arterial blood can be accessed for sampling and for distal limb perfusion and a blood flow and monitoring console may be included in the system.

7 Claims, 3 Drawing Figures

EMERGENCY BYPASS SYSTEM

BACKGROUND OF THE INVENTION

1. Field of the Invention

This invention relates to cardiopulmonary support apparatus and more particularly to a novel closed emergency bypass system having simplicity of operation and economy in use providing inherent advantages as compared with current therapies.

2. Brief Description of the Prior Art

In the past, it has been the conventional practice to employ a plurality of various extracorporeal blood circulation components in blood oxygenation and delivery systems in connection with the care of patients with disease states such as: coronary artery disease, acute atrio-ventricular valve insufficiency, ruptured septum, left ventricular aneurysm. However, prior systems are limited in application and are not used for such diseases as: myocardial infarction, cardiogenic shock, congestive heart failure, septic shock, pulmonary embolus, pulmonary edema, shock lung, chronic obstructive pulmonary disease, adult respiratory distress syndrome, smoke inhalation, drowning and drug overdose.

It is routine practice to employ a conventional membrane-type oxygenator as a major component in a multi-component system as shown in FIG. 3 in the manner described as follows:

Venous blood is accessed through cannulae placed in the superior and inferior vena cavae. This blood is siphoned from the patient through the "patient venous supply" line and into a flexible "venous reservoir" bag. A totally occlusive roller-type "venous pump" propels blood from the venous reservoir bag through a heat exchanger, an oxygenator, and into a flexible "arterial reservoir" bag. The arterial reservoir bag is connected to the venous reservoir bag by a "recirculation line." Another totally occlusive roller-type pump, the "arterial pump," pumps blood from the arterial reservoir bag back to the patient. A third occlusive roller-type pump, the "coronary perfusion pump," propels blood from the arterial reservoir into the root of the aorta to effect cardioplegia. Two more totally occlusive roller-type pumps, the "suction pumps," are used to aspirate blood shed into the pericardial sac or into the pleural spaces, or to evacuate blood from the left ventricular cavity. The final component of the extant circuitry for running the membrane oxygenator is a "water temperature control unit" which pumps water through the heat exchanger.

Problems and difficulties are encountered when employing the conventional oxygenator described above which stem largely from overall complexity and quantity of the various components used in the circuit. For example, at least three blood reservoirs are employed as well as four pumps and attendant tubing and interconnections. Obviously, complicated supervisory requirements and operator expertise are needed and set-up time is substantial. All of these difficulties adversely effect manufacturing cost, patient price, and the number of potential accidental patient hazards.

Therefore, a long standing need has existed to provide a novel means or apparatus for reducing circuit and component complexity whereby inherent advantages are gained as compared with prior and existing cardiopulmonary support systems.

SUMMARY OF THE INVENTION

The above problems and difficulties are obviated by the present invention which provides a novel emergency bypass system for extracorporeal blood circulation which utilizes a minimum number of components operably arranged in a series circuit relationship which includes a venous blood aspiration pump means for introducing a quantity of said venous blood to a membrane-type oxygenator followed by conduction of oxygenated blood to an air or gas bubble trap means and return of the blood to the patient via an arterial connection means. Tubing means interconnects the pump means, the oxygenator, the bubble trap means, and the venous and arterial connection means and a bypass connection is operably and selectively coupled between selected portions of said tubing so that said circuit is in parallel at selected times for pump means and system priming purposes.

Therefore, it is among the primary objects of the present invention to provide an emergency bypass system which contains a non-occlusive-type fluid pump, a gas exchange device, a bubble trapping device, and interconnecting tubing, all of which constitute the entire apparatus employed in the extracorporeal blood circulating system.

Another object of the present invention is to provide a novel emergency bypass system which is closed and has a static extracorporeal fluid volume.

Another object of the present invention is to provide a novel closed cardiopulmonary support apparatus consisting solely of a non-occlusive blood pump, a membrane-type oxygenator, a bubble trapping device, and interconnecting tubing including means for drawing venous blood and returning blood arterially.

Yet another object of the present invention is to provide a novel cardiopulmonary support device which can be internally recirculated via a bypass means for purging air from the system and which includes means for pumping blood over the entire physiologic range.

Yet another object of the present invention is to provide a novel cardiopulmonary support system that may be readily accessed for blood sampling and which is adaptable for mobile use when employed with a pump battery pack and compressed oxygen.

Still a further object of the present invention is to provide a novel emergency bypass system which can be used to rapidly administer large volumes of fluid to a patient undergoing one of a variety of therapeutic procedures wherein such a system acts, in variable degrees, to take over and maintain the functions of the patients' heart and lungs.

Still a further object of the present invention is to provide a novel subsystem which accommodates automatically to changes in patient blood supply and patient blood pressure.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description, taken in connection with the accompanying drawings in which:

DESCRIPTION OF THE PREFERRED EMBODIMENT

Figure 1:
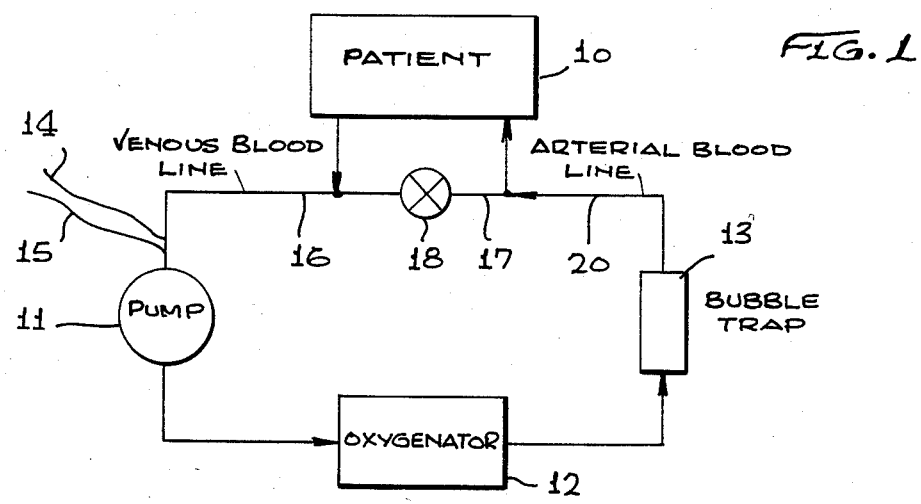
FIG. 1 is a block diagram showing the overall circuit components employed in the emergency bypass system of the present invention.

Referring to the emergency bypass system of the present invention as shown in FIG. 1, a typical technique for application is described as follows: after the patient has been evaluated and established as a suitable candidate for the emergency bypass system, the emergency room physician will initiate a course of action to prepare the patient for cardiopulmonary support. Simultaneously, a nurse or technician will prepare the emergency bypass system circuit employing the components shown in FIG. 1 in which numeral 10 refers to the patient undergoing the procedure, numeral 11 constitutes a pump for extracting venous blood from the patient, numeral 12 represents an oxygenator while numeral 13 constitutes a bubble trap.

The following steps are taken by the emergency room physician in the preparation of the patient and by the nurse or technician in preparing the emergency bypass circuit. Initially, a site is chosen for central access to venous and arterial blood and the area or site is prepared and draped in the conventional manner. A surgical cut down procedure is performed to expose and isolate the appropriate blood vessels. After administering approximately 1 mg/kg body weight Heparin sodium-U.S.P., an appropriate cannula are introduced into the venous and arterial vessels. The venous cannula is to be introduced in an antigrade fashion (relative to blood flow) while the arterial cannula is to be oriented in a retrograde manner. The cannulae are attached to the fully prepared emergency bypass system circuit components with the integral connectors required to establish a continuous blood flow and cardiopulmonary support is initiated.

In preparing the emergency bypass system, the system components are initially removed from a storage box or container and the pump, oxygenator and bubble trap are placed in a series relationship in their respective holding brackets while oxygen flow is initiated at five liters per minute. Two liters of IV solution are attached to a pair of prime spikes 14 and 15 respectively. When the normally closed clamp 19 is opened, the venous line indicated by numeral 16 is primed by means of a bypass loop 17 including a valve or clamp 18 by displacing air with solution while the arterial line 20 is similarly primed until approximately half the bubble trap is primed. Next, the pump head of the pump 11 is primed as well as the oxygenator and connecting tubings until the bubble trap is full. The pump is turned "on" and prime solution is recirculated within the system via the bypass 17 when the valve 18 is open until the system is free of air. The bypass loop 17 is closed by clamp or valve 18 and appropriate tubing lines are handed to the attending physician for attachment to patient cannulae. Upon the physician's order, blood pump speed is increased until a concomitant increases in blood flow cannot be demonstrated. At that point, the blood pump speed is reduced to the lowest speed at which the highest blood flow was achieved. At this time, oxygen flow rate is adjusted to a one to one ratio with blood flow.

Figure 2:
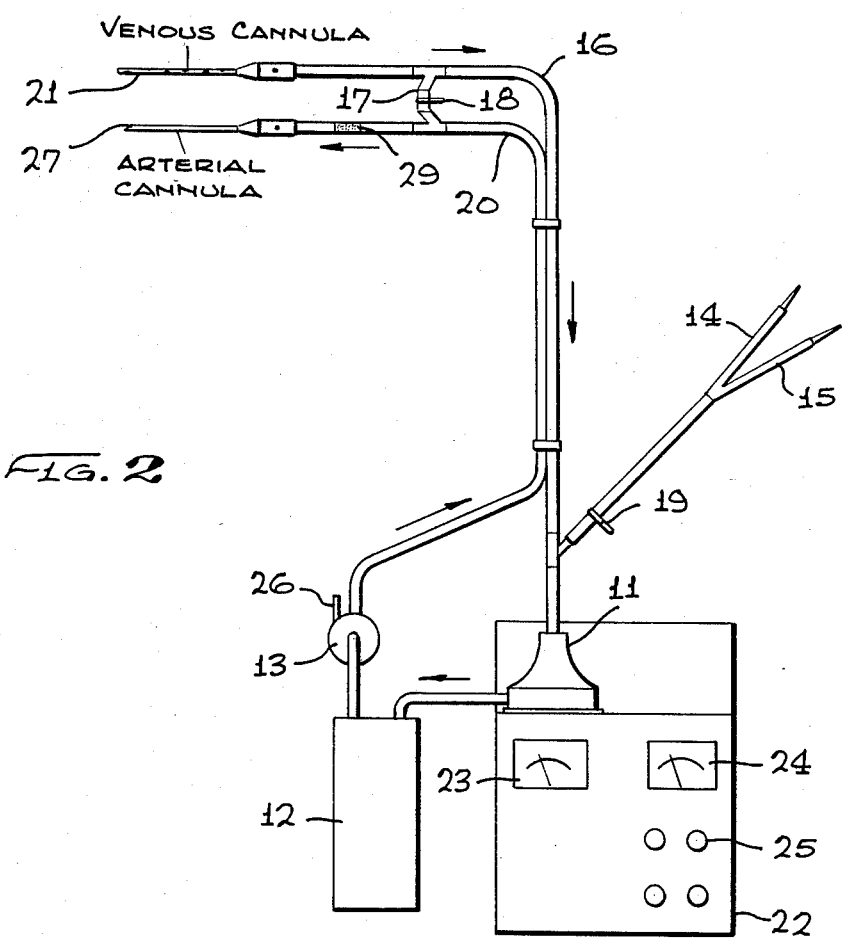
FIG. 2 is a schematic drawing of the components employed in the system shown in FIG. 1.
Figure 3:
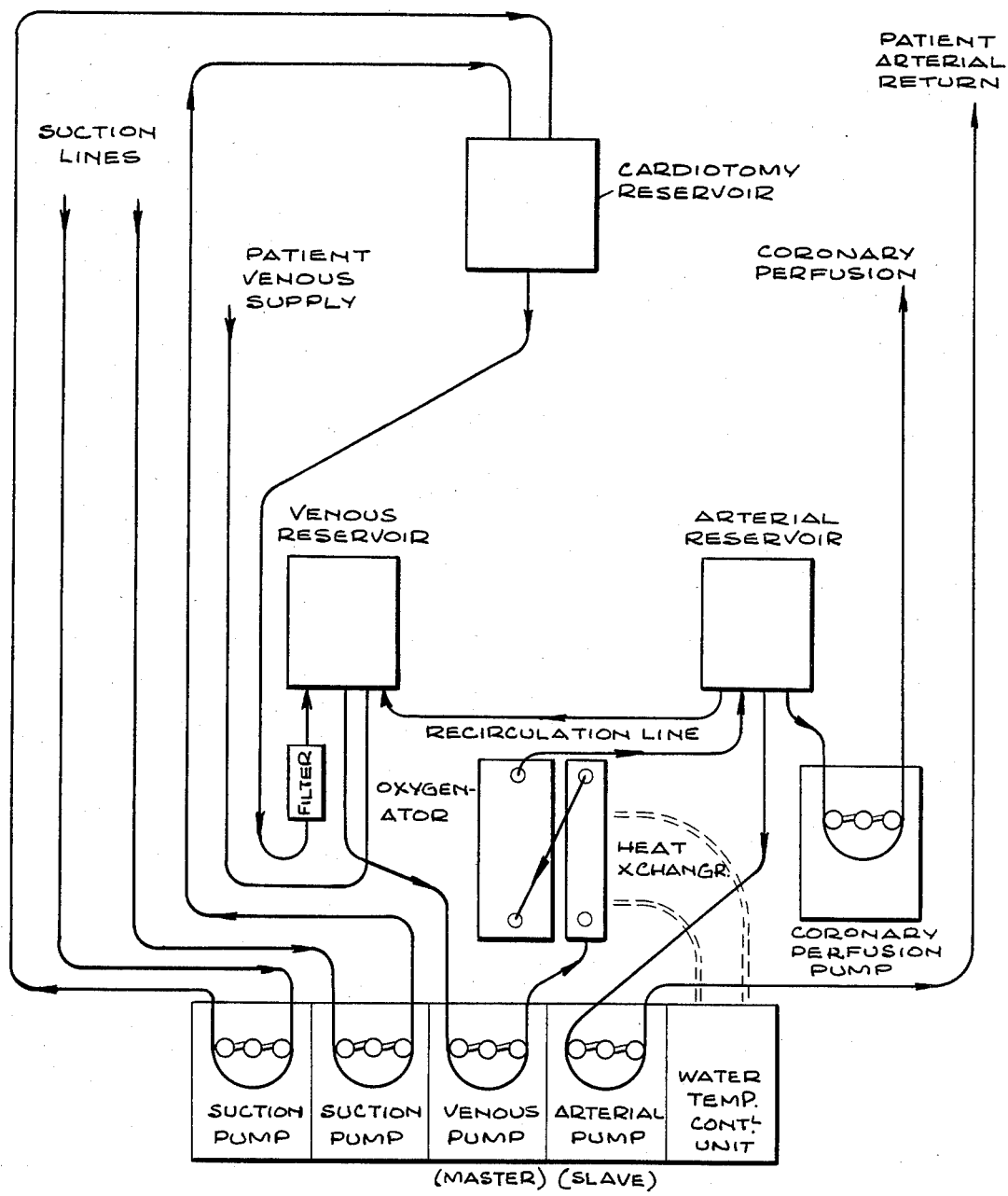
FIG. 3 is a schematic drawing of a conventional multi-component blood oxygenation and delivery system.

Referring now in detail to FIG. 2, a schematic of the system shown in FIG. 1 is illustrated, wherein blood is drawn from the patient via a venous cannulae 21 and introduced to a pump 11 such as a Bio-Pump manufactured by the Bio-Medicus Company in Minneapolis, Minn. Such a pump includes autoregulatory and Atraumatic flow characteristics analogous to the mammalian heart. Preferably, the pump should be used for the sole purpose of extracorporeal circulation. The pump includes rotor cones which are hydrodynamically designed and fabricated from non-thrombogenic acrylics. A magnetic drive and solid housing design prohibits air or contaminent induction. The rotor is mounted on high-quality ball bearings for smooth, dependable operation. By employing hydrodynamic design, the flow path eliminates turbulence, cavitation, and avoids damage to blood elements.

The pump 11 is suitably coupled to a console 22 which may include emergency battery power as protection against power line failure. The console also includes a rpm meter which monitors motor speed of the pump between zero and 4,500 rpm. A flow meter and a range control circuit allow a choice of maximum indicated blood flow of one, five and ten L/min. The rpm meter is indicated by numeral 23 while the flow meter is indicated by numeral 24 while a variety of control knobs such as knob 25 is available for manual handling by the operator. The blood is exited from the pump 11 through the oxygenator 12 which is preferably of the membrane-type and then to the bubble trap 13. The bubble trap includes a purge line 26 for removing air after accumulation in the trap. Blood is then returned to the artery of the patient via a cannulae 27.

For accessing arterial blood in connection with sampling procedures or for distal limb perfusion, a connector 29 is included in the arterial cannula into which a syringe or tubing may be attached.

In view of the foregoing, it can be seen that the utilization of the emergency bypass system of the present invention involves basically three components arranged in series as opposed to approximately 11 or 12 components conventionally utilized in the typical blood oxygenation and delivery system currently employed. As an example, a typical prior art system would include a cardiotomy reservoir as well as a venous and an arterial reservoirs. For moving the blood between the various reservoirs, a master and slave pump system is employed wherein a suction pump, a venous pump, an arterial pump and a coronary perfusion pump is utilized in addition to the oxygenator, heat exchanger and water temperature control unit. Additional filters are incorporated throughtout the system lines and a myriad of tubing and interconnecting components are required. Also, it is extremely difficult to purge the lines and tubing of conventional system of air and other contaminents due to the multiplicity of tubing and connection between the pumps and reservoirs. Therefore, the inventive emergency bypass system of the present invention provides a simpler, convenient and a more controllable system for handling blood flow and patient procedures than conventional systems.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. In a simplified general purpose emergency bypass system having a cardiopulmonary support apparatus withdrawing venous blood from a patient and for patient arterial return thereof, the improvement which consists solely of the combination of:

a closed circuit of components arranged in a series relationship between the patient's venous blood supply and arterial blood return, said circuit having a static extracorporeal fluid volume;

said circuit components consisting of a non-occlusive blood pump, an oxygenator, and interconnecting static extracorporeal volume means providing continuous fluid communication between said components, and said circuit including bubble trapping means;

a venous cannula;

an arterial cannula;

said interconnecting means operably coupled to said venous cannula for withdrawing venous blood into one end of said circuit, and to said arterial cannula at the other end of said circuit for returning blood to the patient; and said closed circuit including a bypass loop selectively coupling said interconnecting means together between said cannulae for priming and air purging purposes in said circuit.

2. In a simplified general purpose emergency bypass system having a cardiopulmonary support apparatus withdrawing venous blood from a patient and for patient arterial return thereof, the improvement which consists solely of the combination of:

a closed circuit of components arranged in a series relationship between the patient's venous blood supply and arterial blood return, said circuit having a static extracorporeal fluid volume;

said circuit components consisting of a non-occlusive blood pump, an oxygenator, and interconnecting static extracorporeal volume means providing continuous fluid communication between said components, and said circuit including bubble trapping means;

a venous cannula;

an arterial cannula;

said interconnecting means operably coupled to said venous cannula for withdrawing venous blood into one end of said circuit, and to said arterial cannula at the other end of said circuit for returning blood to the patient;

said closed circuit including a bypass loop selectively coupling said interconnecting means together between said cannulae for priming and air purging purposes in said circuit; and said closed circuit further including a pair of IV spikes selectively coupled into said interconnecting means between said venous cannula and said blood pump for accessing thereto.

3. In a simplified general purpose emergency bypass system having a cardiopulmonary support apparatus withdrawing venous blood from a patient and for patient arterial return thereof, the improvement which consists solely of the combination of:

a closed circuit of components arranged in a series relationship between the patient's venous blood supply and arterial blood return, said circuit having a static extracorporeal fluid volume;

said circuit components consisting of a non-occlusive blood pump, an oxygenator, and interconnecting static extracorporeal volume means providing continuous fluid communication between said components, and said circuit including bubble trapping means;

a venous cannula;

an arterial cannula;

said interconnecting means operably coupled to said venous cannula for withdrawing venous blood into one end of said circuit, and to said arterial cannula at the other end of said circuit for returning blood to the patient;

said closed circuit including a bypass loop selectively coupling said interconnecting means together between said cannulae for priming and air purging purposes in said circuit; and said circuit components being arranged in a serial placement with said venous cannula coupled to said blood pump, and said oxygenator operably connected between said blood pump and said arterial cannula.

4. In a simplified general purpose emergency bypass system having a cardiopulmonary support apparatus withdrawing venous blood from a patient and for patient arterial return thereof, the improvement which consists solely of the combination of:

a closed circuit of components arranged in a series relationship between the patient's venous blood supply and arterial blood return, said circuit having a static extracorporeal fluid volume;

said circuit components consisting of a non-occlusive blood pump, an oxygenator, and interconnecting static extracorporeal volume means providing continuous fluid communication between said components, and said circuit including bubble trapping means;

a venous cannula;

an arterial cannula;

said interconnecting means operably coupled to said venous cannula for withdrawing venous blood into one end of said circuit, and to said arterial cannula at the other end of said circuit for returning blood to the patient;

said closed circuit including a bypass loop selectively coupling said interconnecting means together between said cannulae for priming and air purging purposes in said circuit; and said blood pump being limited to a centrifugal or an impellor driven pump.

5. In a simplified general purpose emergency bypass system having a cardiopulmonary support apparatus withdrawing venous blood from a patient and for patient arterial return thereof, the improvement which consists solely of the combination of:

a closed circuit of components arranged in a series relationship between the patient's venous blood supply and arterial blood return, said circuit having a static extracorporeal fluid volume;

said circuit components consisting of a non-occlusive blood pump, an oxygenator, and interconnecting static extracorporeal volume means providing continuous fluid communication between said components, and said circuit including bubble trapping means;

a venous cannula;

an arterial cannula;

said interconnecting means operably coupled to said venous cannula for withdrawing venous blood into one end of said circuit, and to said arterial cannula at the other end of said circuit for returning blood to the patient;

said closed circuit including a bypass loop selectively coupling said interconnecting means together between said cannulae for priming and air purging purposes in said circuit, and said blood pump being incorporated into a system monitoring device having at least a flow meter and an rpm meter.

6. In a simplified general purpose emergency bypass system having a cardiopulmonary support apparatus withdrawing venous blood from a patient and for patient arterial return thereof, the improvement which consists solely of the combination of:

a closed circuit of components arranged in a series relationship between the patient's venous blood supply and arterial blood return, said circuit having a static extracorporeal fluid volume;

said circuit components consisting of a non-occlusive blood pump, an oxygenator, and interconnecting static extracorporeal volume means providing continuous fluid communication between said components, and said circuit including bubble trapping means;

a venous cannula;

an arterial cannula;

said interconnecting means operably coupled to said venous cannula for withdrawing venous blood into one end of said circuit, and to said arterial cannula at the other end of said circuit for returning blood to the patient;

said closed circuit including a bypass loop selectively coupling said interconnecting means together between said cannulae for priming and air purging purposes in said circuit;

said closed circuit further including pair of IV spikes selectively coupled into said tubing between said venous cannula and said blood pump for accessing thereto;

said circuit components being arranged in a serial placement with said venous cannula coupled to said blood pump;

said oxygenator operably connected between said blood pump and said arterial cannula;

said blood pump being limited to a centrifugal or impellor driven pump;

said blood pump being incorporated into a system monitoring device having at least a flow meter and an rpm meter; and a connector incorporated into said arterial cannula for accessing arterial blood for sampling or distal limb perfusion.

7. A method of operating a blood cardiopulmonary support apparatus utilizing a minimum number of components not exceeding a pump, an oxygenator, bubble trapping means and static extracorporeal volume means for interconnecting said components in a serial circuit, the steps comprising:

preparing a patient's blood vessels for receiving venous and arterial cannulae;

introducing appropriate cannulae into the venous and arterial vessels;

priming said support apparatus components by displacing air with solution to clear the venous and arterial lines utilizing a bypass loop coupling said venous and arterial lines;

priming the pump, oxygenator and remainder of the interconnecting means until said oxygenator is occupied by solution;

activating said pump to recirculate prime solution until tubing and components are free of air;

clamping said bypass loop followed by connecting said interconnecting means to venous and arterial cannulae; and increasing blood pump speed until a concomitant increase in blood flow cannot be detected, followed by decreasing blood pump speed to the lowest speed at which the highest blood flow was achieved.

* * * * *